US00PP36654P2

(12) United States Plant Patent
Li

(10) Patent No.: US PP36,654 P2
(45) Date of Patent: May 6, 2025

(54) ***PORTULACA* PLANT NAMED 'NUFPO22066'**

(50) Latin Name: *Portulaca oleracea*
Varietal Denomination: NUFPO22066

(71) Applicant: KLEMM + SOHN GMBH & CO. KG, Stuttgart (DE)

(72) Inventor: Ruijun Li, North Parramatta (AU)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/638,143

(22) Filed: Apr. 17, 2024

(51) Int. Cl.
*A01H 5/02* (2018.01)
*A01H 6/00* (2018.01)

(52) U.S. Cl.
USPC ..... Plt./471

(58) Field of Classification Search
USPC ..... Plt./263.1, 471
See application file for complete search history.

(56) References Cited

U.S. PATENT DOCUMENTS

PP32,179 P2 * 9/2020 Koot ..... A01H 5/02
Plt./471

* cited by examiner

*Primary Examiner* — Karen M Redden
(74) *Attorney, Agent, or Firm* — Weatherly IP Solutions, LLC; James M. Weatherly

(57) ABSTRACT

A new *Portulaca* plant particularly distinguished by large white flowers; and early flowering, is disclosed.

1 Drawing Sheet

Genus and species: *Portulaca oleracea.*
Variety denomination: 'NUFPO22066'.

BACKGROUND OF THE NEW PLANT

The present invention comprises a new and distinct variety of *Portulaca*, botanically known as *Portulaca oleracea*, and hereinafter referred to by the variety name 'NUFPO22066'. 'NUFPO22066' originated from a cross-pollination conducted in December 2018 in Cobbitty, New South Wales, Australia between the proprietary female *Portulaca* variety '18.80.29' (unpatented) and the proprietary male *Portulaca* variety '18.80.37' (unpatented).

The seeds from the cross were sown and plants were grown for evaluation, where an individual plant designated 'NUFPO22066' was selected from the group of plants in Cobbitty, New South Wales, Australia in October 2019.

In December 2019, 'NUFPO22066' was first vegetatively propagated by vegetative cuttings in Cobbitty, New South Wales, Australia. 'NUFPO22066' was found to reproduce true to type in successive generations of asexual propagation via vegetative cuttings.

SUMMARY

The following are the most outstanding and distinguishing characteristics of this new variety when grown under normal horticultural practices in Cobbitty, New South Wales, Australia.

1. Large white flowers; and
2. Early flowering.

DESCRIPTION OF THE PHOTOGRAPH

This new *Portulaca* plant is illustrated by the accompanying photograph which shows the plant's overall plant habit including form, buds, foliage, and flowers. The photograph is of a plant approximately 20-weeks-old grown outdoors in Stuttgart, Germany in August 2022. The colors shown are as true as can be reasonably obtained by conventional photographic procedures.

DESCRIPTION OF THE NEW VARIETY

The following detailed descriptions set forth the distinctive characteristics of 'NUFPO22066'. The data which define these characteristics were collected from asexual reproductions carried out in Cobbitty, New South Wales, Australia. Data was collected on three-month-old plants grown in 2020. Color references are to The R.H.S. Colour Chart of The Royal Horticultural Society of London (R.H.S.), 5$^{th}$ edition (2007).

Classification:
- *Family.*—Portulacaceae.
- *Botanical.*—*Portulaca oleracea.*
- *Common.*—Purslane.
- *Designation.*—'NUFPO22066'.

Parentage:
- *Female parent.*—'18.80.29' (unpatented).
- *Male parent.*—'18.80.37' (unpatented).

Plant:
- *Habit and form.*—Compact and spreading.
- *Height.*—3.2 cm.
- *Spread.*—26.0 cm.
- *Time and conditions to produce a rooted cutting.*—5 to 8 days.
- *Life cycle.*—Annual.
- *Flowering requirements.*—Spring to Autumn.

Stems:
- *General description.*—Round with slight ridges.
- *Stem color.*—RHS 145A.
- *Anthocyanin color.*—Absent.

*Pubescence*.—Absent.
*Stem diameter*.—0.27 cm.
*Stem length*.—14.0 cm to 20.0 cm.
*Internode length*.—1.8 cm.
*Branching*.—Abundant.

Leaves:
*Arrangement*.—Alternate, simple.
*Shape*.—Obovate.
*Apex*.—Acute.
*Base*.—Rounded.
*Margin*.—Entire.
*Leaf attachment*.—Petiolate.
*Leaf length*.—1.9 cm.
*Leaf width*.—1.1 cm.
*Leaf thickness*.—0.15 cm.
*Texture*.—Upper surface: Smooth, glabrous, succulent. Lower surface: Smooth, glabrous, succulent.
*Leaf color*.—Upper surface: RHS 137B. Lower surface: RHS 138B.
*Leaf surface pubescence*.—Absent.
*Venation*.—Pinnate.
*Petiole*.—Length: 0.2 cm. Diameter: 0.15 cm. Color: RHS 145B.
*Fragrance*.—None detected.

Inflorescence:
*Inflorescence type*.—Solitary, sessile.
*Flowering habit*.—Freely flowering habit and most flowers face upright.
*Time to bloom from propagation*.—Approximately 8 weeks.
*Lastingness of individual blooms on the plant*.—One day.
*Flower diameter*.—2.9 cm.
*Flower depth*.—1.2 cm.
*Fragrance*.—None detected.

Flower bud:
*Shape*.—Ovoid.
*Bud length*.—0.9 cm.
*Bud diameter*.—0.6 cm.
*Bud color*.—RHS 144A.

Corolla:
*Shape*.—Obovate.
*Petal pubescence*.—Smooth, glabrous.
*Petal size*.—Length: 1.4 cm. Width: 1.0 cm.
*Petal apex*.—Emarginate.
*Petal margin*.—Entire.
*Petal color*.—Upper surface: RHS NN155D. Lower surface: RHS NN155D.

Calyx:
*Arrangement*.—Two and base fused.
*Sepals*.—Shape: Deltoid. Apex: Acute. Margin: Entire. Sepal length: 0.8 cm. Sepal diameter: 0.6 cm. Sepal color: RHS 146D. Texture: Upper surface: Smooth. Lower surface: Smooth. Appearance: Double lobed Reproductive organs: Androecium.
*Stamen number*.—About 75.
*Stamen form*.—Free.
*Anther*.—RHS 17A.
*Filament*.—RHS 145D.
*Stamen length*.—0.6 cm.
*Pollen amount*.—Abundant.
*Pollen color*.—RHS 23A.
*Fragrance*.—Absent.
*Pistil number*.—1.
*Pistil length*.—1.3 cm.
*Stigma color*.—RHS 155D.
*Stigma length*.—0.3 cm.
*Style length*.—1.0 cm.
*Style color*.—RHS 145D.
*Seed production*.—About 20 seeds per flower.
*Seed diameter*.—1.0 mm.
*Seed colour*.—RHS 200B.

Disease and insect resistance: Neither resistance nor susceptibility to diseases or insects has been observed.

COMPARISON WITH PARENTAL LINES AND KNOWN VARIETY

'NUFPO22066' is distinguished from its parents as described in Table 1.

TABLE 1

Comparison with Parental Lines

| Characteristic | Variety 'NUFPO22066' | Female parent '18.80.29' | Male Parent '18.80.37' |
|---|---|---|---|
| Flower size | 2.9 cm | 2.7 cm | 3.0 cm |
| Flower colour | White | White | Pink blush |

'NUFPO22066' is most similar to the commercial *Portulaca* variety Duna® White (patent status unknown). Differences between the varieties are described in Table 2.

TABLE 2

Comparison with Similar Variety

| Characteristic | Variety 'NUFPO22066' | Commercial line Duna ® White (patent status unknown) |
|---|---|---|
| Earliness | 3 to 4 days earlier than Duna White | 3 to 4 days later than NUFPO22066 |
| Flower size | 2.9 cm | 2.7 cm |

I claim:

1. A new and distinct cultivar of *Portulaca* plant designated 'NUFPO22066' as illustrated and described herein.

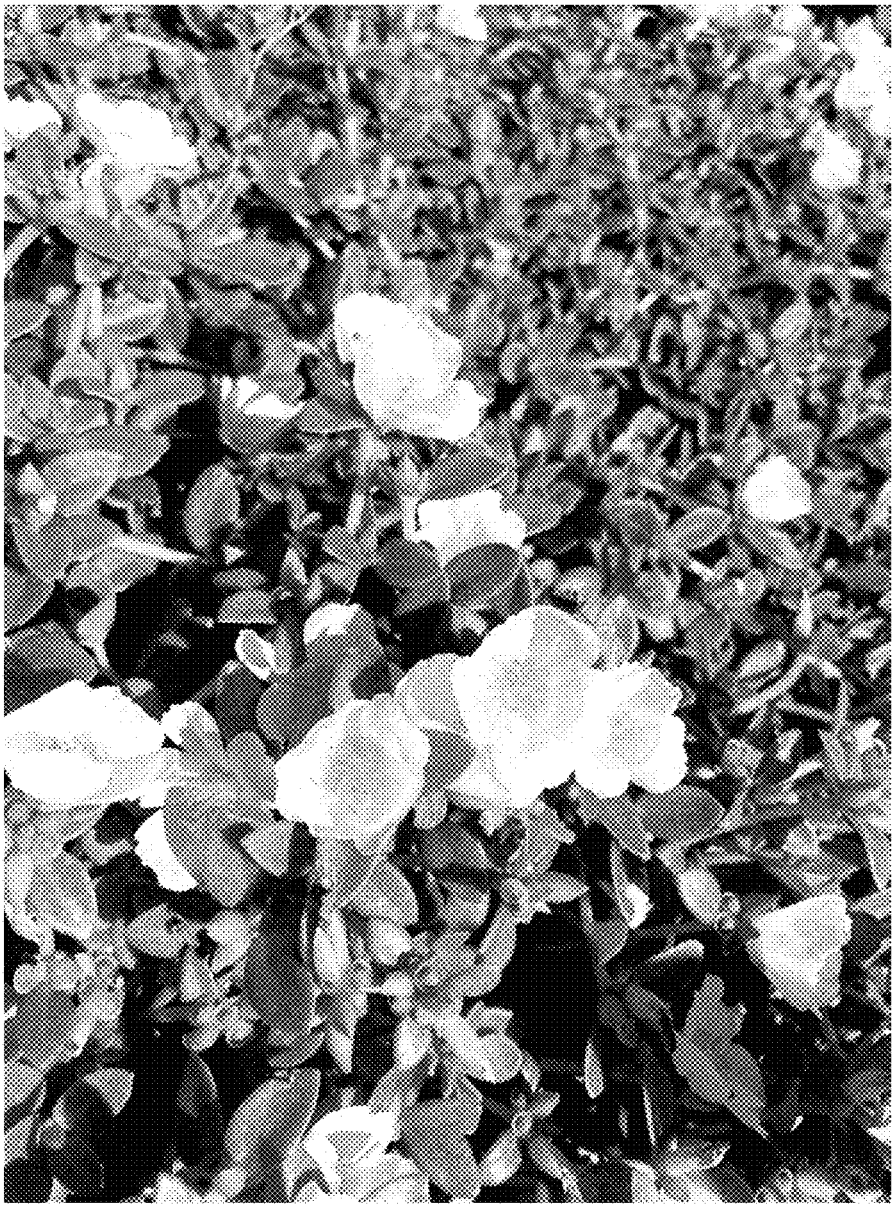

* * * * *